(12) United States Patent
LaFontaine

(10) Patent No.: US 8,133,264 B1
(45) Date of Patent: Mar. 13, 2012

(54) THERAPEUTIC HEATING SLEEVE

(76) Inventor: Ronald P. LaFontaine, Simi Valley, CA (US)

( * ) Notice: Subject to any disclaimer, the term of this patent is extended or adjusted under 35 U.S.C. 154(b) by 1177 days.

(21) Appl. No.: 11/975,629

(22) Filed: Oct. 22, 2007

(51) Int. Cl.
*A61F 7/00* (2006.01)
(52) U.S. Cl. ............... 607/112; 219/211; 2/59; 2/125
(58) Field of Classification Search .............. 219/211; 607/112; 2/59, 125
See application file for complete search history.

(56) References Cited

U.S. PATENT DOCUMENTS

| | | | | |
|---|---|---|---|---|
| 2,329,766 | A * | 9/1943 | Jacobsen ................ | 219/211 |
| 2,948,802 | A * | 8/1960 | Shaw .................... | 219/212 |
| 3,084,241 | A * | 4/1963 | Carrona ................. | 219/211 |
| 3,178,559 | A * | 4/1965 | Fogel et al. ............ | 219/527 |
| 3,501,616 | A * | 3/1970 | Arron ................... | 219/211 |
| 3,748,436 | A * | 7/1973 | Cossaboom ............. | 219/211 |
| 4,026,299 | A * | 5/1977 | Sauder .................. | 607/104 |
| 4,356,570 | A * | 11/1982 | Vernon et al. ........... | 2/16 |
| 4,404,460 | A | 9/1983 | Kerr | |
| 4,736,088 | A | 4/1988 | Bart | |
| 4,747,409 | A * | 5/1988 | Silen .................... | 607/108 |
| 4,764,665 | A | 8/1988 | Orban et al. | |
| 4,977,622 | A * | 12/1990 | Schley .................. | 2/59 |
| 4,985,934 | A * | 1/1991 | Perry .................... | 2/125 |
| 5,032,705 | A * | 7/1991 | Batcheller et al. ....... | 219/211 |
| 5,035,001 | A * | 7/1991 | Novick .................. | 2/125 |
| 5,436,429 | A * | 7/1995 | Cline ................... | 219/202 |
| 5,451,747 | A * | 9/1995 | Sullivan et al. ......... | 219/528 |
| 5,839,043 | A | 11/1998 | Okabayashi et al. | |
| 5,909,801 | A * | 6/1999 | Coffman ................ | 2/16 |
| 6,052,824 | A * | 4/2000 | May ..................... | 2/16 |
| 6,237,151 | B1 * | 5/2001 | Dellinger ............... | 2/69 |
| 6,550,471 | B2 | 4/2003 | Szymocha et al. | |
| 6,622,529 | B1 | 9/2003 | Crane | |
| 6,649,886 | B1 | 11/2003 | Kleshchik | |
| 6,996,848 | B2 * | 2/2006 | Donaldson ............. | 2/16 |
| 7,230,206 | B1 * | 6/2007 | Randall ................. | 219/211 |
| 39,845 | A1 * | 1/2009 | Hadash ................. | 2/16 |
| 2007/0023417 | A1 * | 2/2007 | Keane ................... | 219/494 |
| 2007/0162096 | A1 * | 7/2007 | Zakuto et al. ........... | 607/104 |
| 2007/0283516 | A1 * | 12/2007 | Rasmussen et al. ...... | 15/160 |
| 2009/0054959 | A1 * | 2/2009 | Felker .................. | 607/111 |
| 2009/0099631 | A1 * | 4/2009 | Augustine et al. ....... | 607/104 |
| 2009/0216305 | A1 * | 8/2009 | Bonner ................. | 607/108 |
| 2011/0152983 | A1 * | 6/2011 | Schirrmacher et al. ... | 607/104 |

* cited by examiner

*Primary Examiner* — Roy Gibson
*Assistant Examiner* — Kaitlyn Smith
(74) *Attorney, Agent, or Firm* — Albert O. Cota

(57) ABSTRACT

A therapeutic heating sleeve (10) consisting of a laminate pad (20) with an exterior cover (22), a batting (24), a polyester lining (26), a heating wire (28) and an interior lining (30) having a hook and loop fastener (32) that is attached on the exterior cover (22) and the interior lining (30). The laminate pad (20) has a lower portion that is in the shape of a human arm and an upper portion that is in the shape of a human shoulder. The heating sleeve (10) is completed by overlapping the pad's right side onto the pad's left side and attaching the two sides with the hook and loop fastener (32), thereby forming an open-ended sleeve. An electrical control is removably attached to the laminate pad (20) for applying electrical energy to the heating wire (28), thereby creating heat for baseball pitchers to warm up their arm and shoulder prior to pitching.

15 Claims, 2 Drawing Sheets

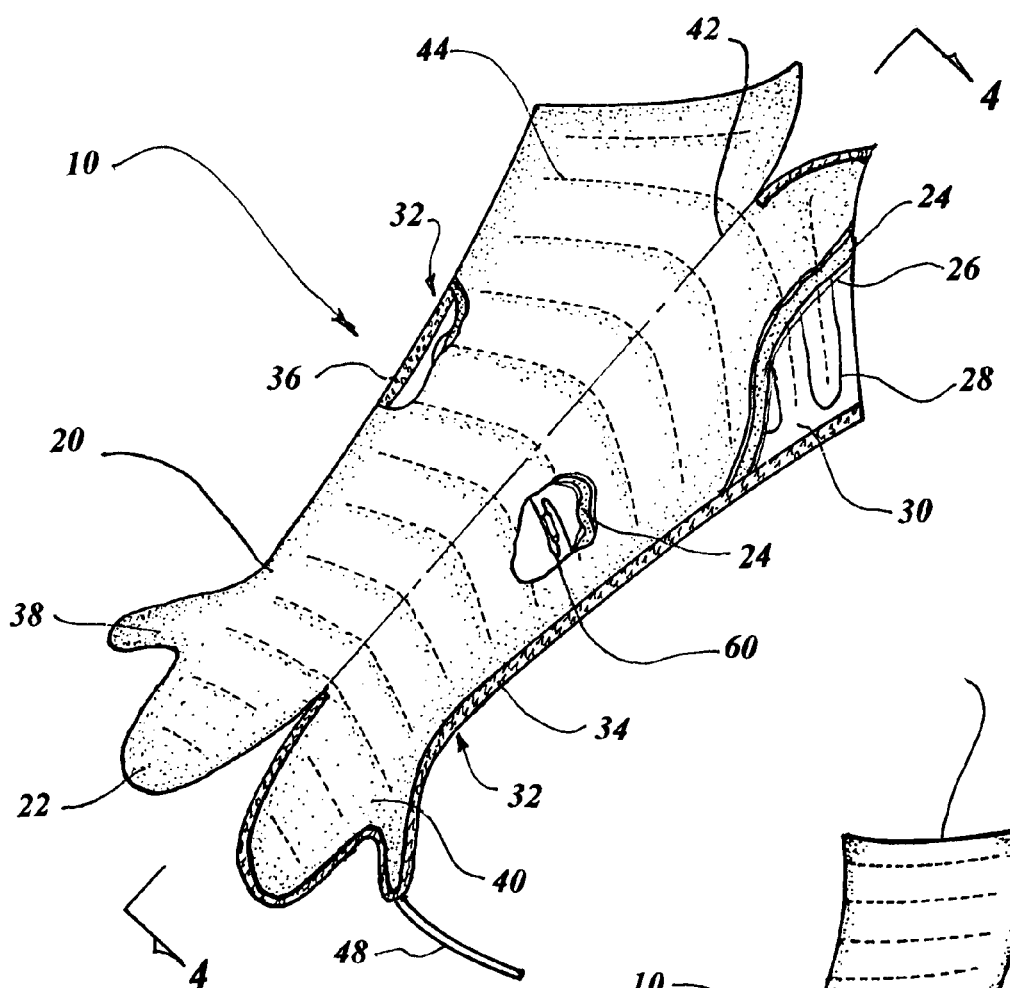
FIG. 3
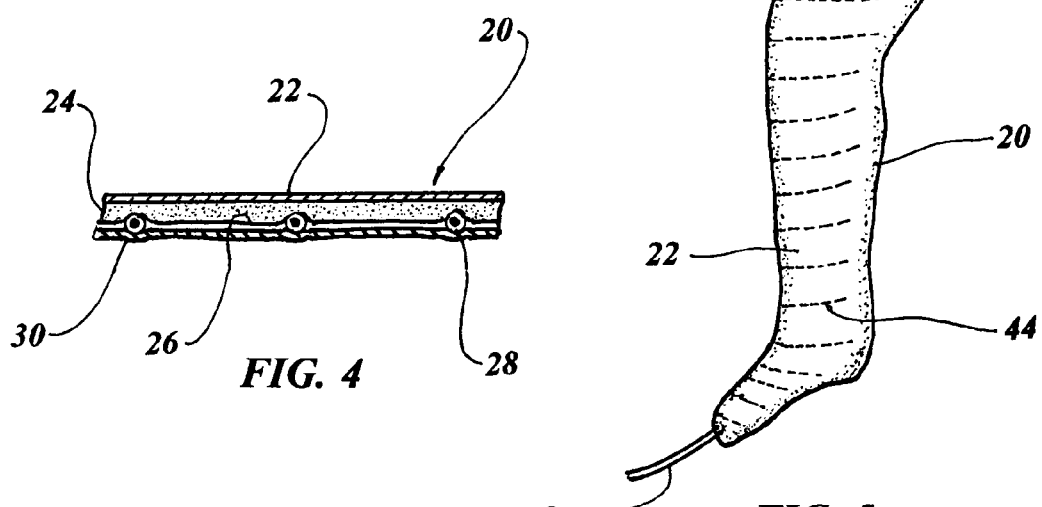
FIG. 4
FIG. 5

THERAPEUTIC HEATING SLEEVE

TECHNICAL FIELD

The invention generally pertains to heating pads and more specifically to a therapeutic heating sleeve that covers a person's arm and shoulder area. The heating sleeve is particularly effective for baseball pitchers to warm up their arm prior to pitching.

BACKGROUND ART

Heating pads have been in use for therapeutic medical purposes for many decades. Typically, a heating pad provides heat to various parts of a body for warming, pain relief and healing purposes. In the prior art, heating pads have a square or rectangular shape and may include straps for wrapping and holding the pad around limbs or other areas where the heat is directed. Specialized pads have been developed for specific purposes such as the hands in the form of gloves or a muff. Even heated clothing that covers a person's body has been developed for use in cold environments. However in the prior art a therapeutic heating sleeve that is particularly designed for use by an athlete to warm his or her arm and shoulders prior to going into the playing field was not located.

A search of the prior art did not disclose any patents that possess the novelty of the instant invention, however the following U.S. patents are considered related:

| Pat. No. | Inventor | Issue Date |
| --- | --- | --- |
| 4,404,460 | Kerr | Sep. 13, 1983 |
| 4,736,088 | Bart | Apr. 5, 1988 |
| 4,764,665 | Orban et al. | Aug. 16, 1988 |
| 5,839,043 | Okabayashi et al. | Nov. 17, 1998 |
| 6,622,529 | Crane | Sep. 23, 2003 |
| 6,649,886 | Kleshchik | Nov. 18, 2003 |

Kerr in U.S. Pat. No. 4,404,460 discloses a heat controlled clothing having multiple sections that are adapted to cover different areas of the human body. Electrical wires are employed which include bus wires and heater wires with circuitry controlling battery powered current flow.

U.S. Pat. No. 4,736,088 issued to Bart discloses a therapeutic heating pad having a laminate structure which concentrates the flow of heat in one direction. The laminate structures in the form of a flannel material, which is held in a tubular configuration to form a muff for fomentation of a body member inserted therein.

Orban et al. in U.S. Pat. No. 4,764,665 discloses a heated glove that includes an electrically-heated woven fabric. The fabric is coated with electrically conducting metal to enable its use as a heating element.

Okabayashi et al. in U.S. Pat. No. 5,839,043 discloses an induction heating fixing sleeve that is formed of a flexible thin electrically-conductive magnetic material in a coil, thereby producing eddy currents in the sleeve to generate heat.

U.S. Pat. No. 6,622,529 B1 issued to Crane discloses a personal dry-cleaning apparatus having a housing, a wetting means and sources of heat to form steam to be generated within a clothing bag.

Kleshchik in U.S. Pat. No. 6,649,886 B1 discloses a highly flexible and reliable electric heating cloth and method for providing a stable elevated temperature to an environmental site. The heating cloth consists of conductive resistive threads which are interwoven with non-conductive threads.

For background purposes and as indicative of the art to which the invention is related reference may be made to the remaining cited patent issued to Szymocha et al. in U.S. Pat. No. 5,550,471.

DISCLOSURE OF THE INVENTION

The therapeutic heating sleeve is primarily designed to provide a heating sleeve that covers a person's arm and shoulder area. The invention is particularly designed for use by athletes and especially baseball pitchers, to warm up their arm and shoulder prior to pitching. Since the game of baseball has become popular, there is a need to quickly heat up a pitcher's arm without requiring the pitcher to warm up their arm by repeatedly throwing a baseball, applying heat by means of a fan or by wrapping hot towels around the arm and shoulder. The instant invention solves this heat-applying need by the use of external heat in the form of electrical energy converted into heat through the use of a resistance wire that heats up and dissipates heat directly to the pitcher's arm and shoulder. By placing the invention onto the pitcher's arm and shoulders, the heat produced decreases the time required to warm-up the critical areas.

An important object of the invention is that the heating sleeve is easy to use, as the entire arm is slid into the open end of the sleeve and simply plugged into an electrical outlet provided at most ball parks.

Another object of the invention is that the heat may be adjusted to the level desired by the individual player, thereby providing the necessary comfort and still achieving quick warm-up time.

Still another object of the invention is that conventional utility power can be used to operate the therapeutic hearing pad.

These and other objects and advantages of the present invention will become apparent from the subsequent detailed description of the preferred embodiment and the appended claims taken in conjunction with the accompanying drawings.

BRIEF DESCRIPTION OF THE DRAWINGS

FIG. 3 is a plan view of the therapeutic heating sleeve in the preferred embodiment spread out in the flat.

FIG. 4 is a partial cross-sectional view taken along lines 4-4 of FIG. 3 indicating the internal layers of the therapeutic heating sleeve.

FIG. 5 is a partial isometric view of the therapeutic heating sleeve in the second embodiment in the shape of a person's leg.

BEST MODE FOR CARRYING OUT THE INVENTION

Figure 1:
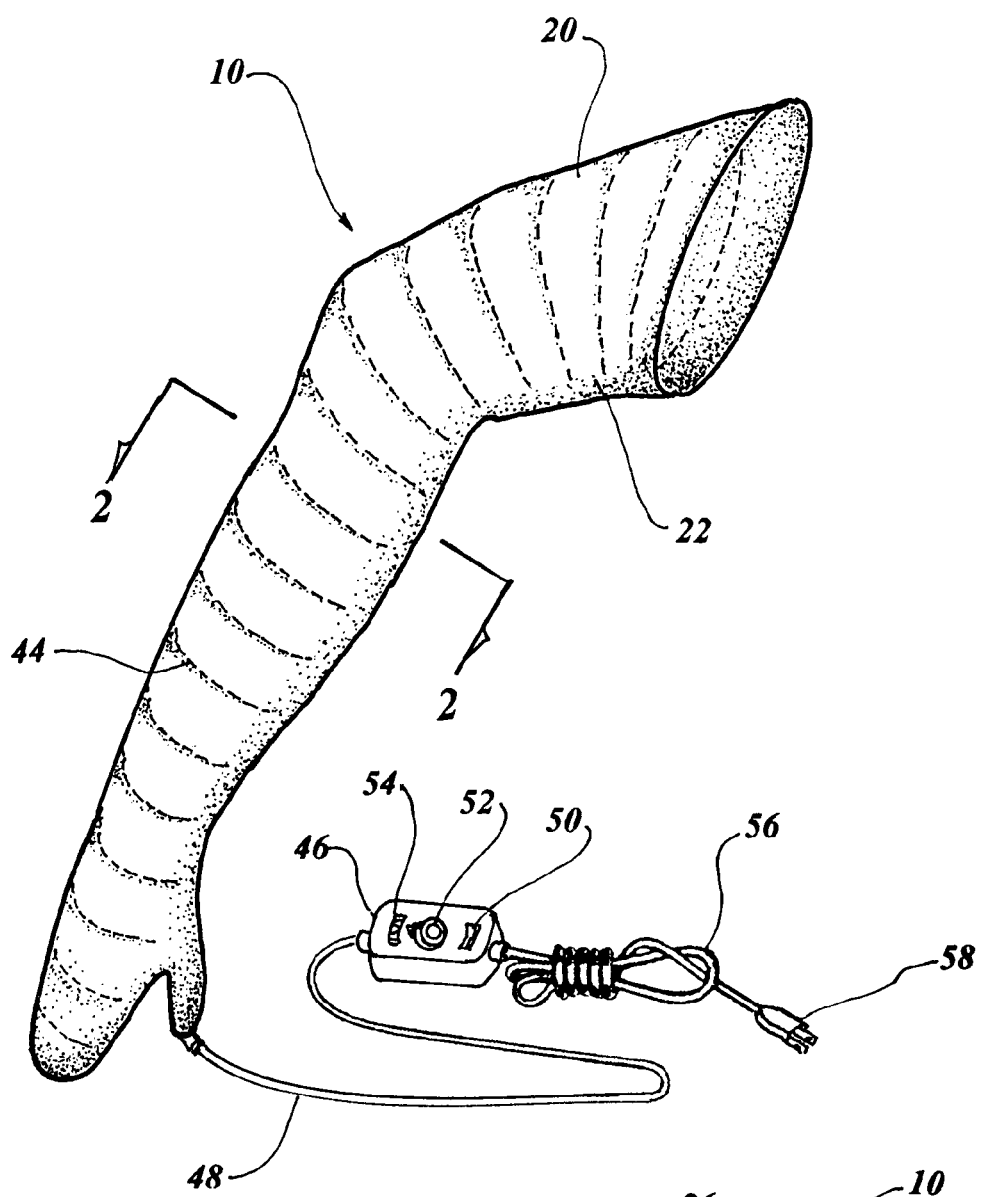
FIG. 1 is a partial isometric view of the therapeutic heating sleeve in the preferred embodiment.

The best mode for carrying out the invention is presented in terms of a preferred embodiment and a second embodiment for a therapeutic heating sleeve 10. The preferred embodiment, as shown in FIGS. 1 through 4, is comprised of a laminate pad 20 having an exterior cover 22. The cover 22 is further comprised of a woven fabric cloth lamina that is fabricated from a material that is treated to be non-flammable, such as cotton cloth, cotton and polyester blend cloth, rip-stop nylon, neoprene coated polyester, chlorosulfated polyethylene coated nylon, nylon infused with silicone or woven nylon.

The laminate pad 20 incorporates an insulating batting lamina 24 that is disposed onto the exterior cover 22 for retaining heat within the sleeve 10. The batting 24 is preferably comprised of a non-flammable polyester material having a thickness ranging from 0.25 inches to 0.75 inches (6.35 cm to 1.9 cm).

A polyester lining 26 is disposed onto the insulating batting lamina 24 with a flexible resistance heating wire 28 located in a winding path onto the polyester lining 26 for supplying heat within the sleeve 10. The heating wire 28 preferably consists of a nichrome wire having a thermoplastic sheath such as a vinyl, nylon or polyester material having a diameter from 0.008 inches to 0.010 inches (0.2 mm to 0.25 mm).

Figure 2:
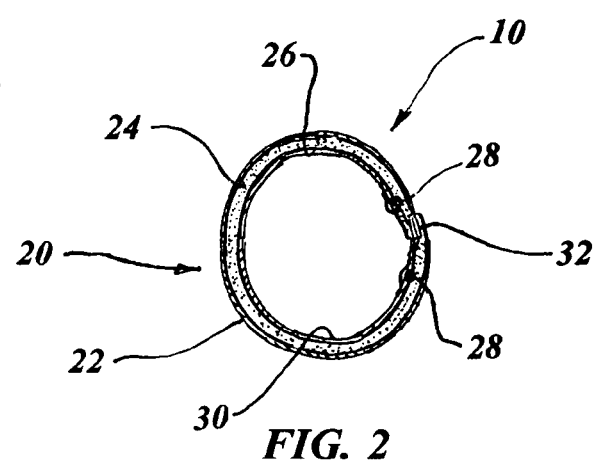
FIG. 2 is a cross-sectional view taken along lines 2-2 of FIG. 1.

A soft woven fabric interior lining 30 is disposed on the heating wire 28, and preferably consists of a non-flammable cotton flannel material. A length of a hook and loop fastener 32 is attached by sewing, bonding with adhesive, or heat sealing. The fastener 32 is placed in opposed positions on the outer surface of the exterior cover 22 and the interior lining 30 through the insulating batting lamina 24 and polyester lining 26. The hook portion 34 of the hook and loop fastener 32 is on one side and the loop portion 36 is on the opposite side, as shown in FIG. 3. FIGS. 2-4 illustrate the laminate pad's 20 layered construction and FIG. 1 shows the heating sleeve 10 having a lower portion configured in the shape of a human arm and an upper portion having a shape of a human shoulder. FIG. 3 illustrates the sleeve 10 in its flattened, or spread out flat, configuration which is an exact duplicate of the sleeve's arm shape having a right side 38 and a left side 40, with a fold line 42 in the middle illustrated as a phantom line. FIG. 1 also shows the therapeutic heating sleeve 10 in its complete form with the laminate pad right side 38 folded onto the laminate left side 40 overlapping the hook and loop fastener 32 together forming an open-ended sleeve.

The laminate pad 20 is sewn together in a quilting fashion with stitching 44 between the serpentine path of the heating wire 28 to maintain the wire's location and to provide additional structural integrity to the pad 20.

An electrical control is removably attached to the laminate pad 20 for applying electrical energy to the resistance heating wire 28, thereby creating heat for baseball pitchers to warm up their arm and shoulder prior to pitching. The electrical control includes a control module 46 that is attached to the heating sleeve 10 with a first flexible electrical cord 48.

The control module 46 includes an on/off switch 50, a heat selection dial 52, temperature selection indicia 54 adjacent to the heat selection dial 52, and a second flexible cord 56 that extends from the control module 46 and terminates with an electrical plug 58, as shown in FIG. 1, that is typically inserted into a utility power outlet.

At least one high temperature thermostat 60, as illustrated in FIG. 3, is connected in series with the flexible heating wire 28 to automatically break continuity of the wire 28 when the wire temperature exceeds a predetermined limit and to return continuity when the wire temperature reaches a safe level.

The second embodiment of a heating sleeve 62, as illustrated in FIG. 5, consists of the same elements as described in the preferred embodiment except the heating sleeve 10 is configured in the shape of a human leg, thereby creating heat for an athlete's leg.

While the invention has been described in detail and pictorially shown in the accompanying drawings, it is not to be limited to such details, since many changes and modifications may be made to the invention without departing from the spirit and scope thereof. Hence, it is described to cover any and all modifications and forms which may come within the language and scope of the appended claims.

The invention claimed is:

1. A therapeutic heating sleeve comprising:
   a) a laminate pad having:
      1) an exterior cover of a woven fabric cloth lamina,
      2) an insulating batting lamina, disposed onto the exterior cover for retaining heat within the sleeve,
      3) a polyester lining disposed onto the insulating batting lamina,
      4) a flexible resistance heating wire disposed in a winding path onto the polyester lining for supplying heat within the sleeve,
      5) a soft woven fabric interior lining disposed on the heating wire, and
      6) a length of hook and loop fastener that is attached in opposed positions on an outer surface of the exterior cover and the interior lining through the insulating batting and polyester lining, wherein said laminate pad having a lower portion in the shape of a human arm and an upper portion in the shape of a human shoulder with each portion having a right side and a left side, with the therapeutic heating sleeve completed by juxtapositioning the laminate pad right side onto the laminate left side and overlapping the hook and loop fastener together, thereby forming an open-ended sleeve, and
   b) an electrical control that is removably attached to said laminate pad for applying electrical energy to the resistance heating wire, thereby creating heat for baseball pitchers to warm up their arm and shoulder prior to pitching.

2. The therapeutic heating sleeve as recited in claim 1 wherein said exterior cover is fabricated of a non-flammable material that is selected from the group consisting of cotton cloth, cotton and polyester blend cloth, rip-stop nylon, neoprene coated polyester, chlorosulfated polyethylene coated nylon, nylon infused with silicone and woven nylon.

3. The therapeutic heating sleeve as recited in claim 1 wherein said insulating batting material further comprises a non-flammable polyester material.

4. The therapeutic heating sleeve as recited in claim 1 wherein said insulating batting further comprises a thickness from 0.25 inches to 0.75 inches (6.35 cm to 1.9 cm).

5. The therapeutic heating sleeve as recited in claim 1 wherein said flexible resistance heating wire further comprises a nichrome wire with a thermoplastic sheath selected from the group consisting of vinyl, nylon and polyester.

6. The therapeutic heating sleeve as recited in claim 1 wherein said flexible resistance heating wire further having a diameter from 0.008 inches to 0.010 inches (0.2 mm to 0.25 mm).

7. The therapeutic heating sleeve as recited in claim 1 wherein said woven fabric interior lining further comprising a non-flammable cotton flannel material.

8. The therapeutic heating sleeve as recited in claim 1 wherein the length of the hook and loop fastener is attached by a method selected from the group consisting of sewing, bonding with adhesive and heat sealing.

9. The therapeutic heating sleeve as recited in claim 1 wherein said laminate pad is sewn together in a quilting fashion with stitching between the winding path of the heating wire to maintain the wire's location and to provide structural integrity to the pad.

10. The therapeutic heating sleeve as recited in claim 1 wherein said electrical control is further comprised of a control module that is attached to the heating sleeve with a first flexible electrical cord.

11. The therapeutic heating sleeve as recited in claim 10 wherein said control module further comprises an on/off switch.

12. The therapeutic heating sleeve as recited in claim 11 wherein said control module further comprises a heat selection dial.

13. The therapeutic heating sleeve as recited in claim 12 wherein said control module further comprises temperature selection indicia that is located adjacent to said heat selection dial.

14. The therapeutic heating sleeve as recited in claim 10 wherein said control module further comprises a second flexible electrical cord that extends from said control module to an electrical plug.

15. The therapeutic heating sleeve as recited in claim 1 wherein said electrical control further comprise at least one high temperature thermostat within the flexible heating wire to automatically break continuity of the wire when the wire temperature exceeds a predetermined limit and to return continuity when the wire temperature attains a safe level.

* * * * *